United States Patent [19]

Loozen

[11] Patent Number: 4,628,044
[45] Date of Patent: Dec. 9, 1986

[54] LHRH ANTAGONISTS

[75] Inventor: Hubert J. J. Loozen, Uden, Netherlands

[73] Assignee: Akzo N.V., Netherlands

[21] Appl. No.: 641,194

[22] Filed: Aug. 16, 1984

[30] Foreign Application Priority Data

Aug. 16, 1983 [NL] Netherlands ............... 8302875
Jan. 18, 1984 [NL] Netherlands ............... 8400153

[51] Int. Cl.$^4$ .................. A61K 37/43; C07K 7/20
[52] U.S. Cl. .............................. 514/15; 530/313; 514/800
[58] Field of Search ............. 260/112.5 R; 514/15; 530/313; 514/800

[56] References Cited

FOREIGN PATENT DOCUMENTS 0081877 6/1983 European Pat. Off. .

Primary Examiner—Delbert R. Phillips
Attorney, Agent, or Firm—Wegner & Bretschneider

[57] ABSTRACT

The invention relates to novel peptides and peptide derivatives which act as antagonists of natural LH-RH and have the general formula:

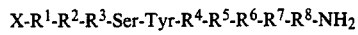

$$X-R^1-R^2-R^3-Ser-Tyr-R^4-R^5-R^6-R^7-R^8-NH_2$$

wherein
 X represents hydrogen or a lower acyl(1–6 C) group,
 $R^1$ and $R^2$ represent either the same or different groups selected from D-Bal(2), D-Bal(3), D-Nal(1), D-Nal(2), D-Phe or D-Phe substituted at the phenyl moiety by one or more halogen, alkyl(1–4 C), alkoxy (1–4 C) or nitro groups;
 $R^3$ represents D-Trp, D-Bal(2), D-Bal(3), D-Nal(1), D-Nal(2) or D-Pal, with the proviso that at least one of the symbols $R^1$ and $R^3$ represents a D-Bal(2) or D-Bal(3) group;
 $R^4$ represents D-Arg, D-Lys, D-homo Arg or D-dialkyl (1–4 C)-homo Arg;
 $R^5$ represents L-Leu, L-Met or the alkyl(1–4C) or phenylalkyl(7–10C) ether of L-Cys, L-Ser or L-homo Ser;
 $R^6$ represents L-Lys or L-Arg;
 $R^7$ represents L-Pro or L-thiaprolyl, and
 $R^8$ represents D-Ala or Gly.

The invention also includes the acid addition salts of the above defined peptides.

4 Claims, No Drawings

LHRH ANTAGONISTS

The invention relates to novel peptides and peptide derivatives which act as antagonists of natural LH-RH (luteinising hormone releasing hormone, which possesses the following aminoacid sequence:

p-Glu-His-Trp-Ser-Tyr-Gly-Leu-Arg-Pro-Gly-NH$_2$).

The invention also relates to methods for the preparation of the novel peptides and to a pharmaceutical compostion which contains these substances as the active constituent.

For a number of years efforts have already been made to produce selective and very potent antagonists of LH-RH by modification of the original LH-RH molecule. The interest in this type of antagonist is explained by the fact that the LH-RH antagonists can be employed not only in the endocrine sector but also in the treatment of various sorts of cancer.

Particularly active LH-RH antagonists are known and described in European Published Pat. No. 81,877.

There have now been found novel peptides having an interesting LH-RH antagonistic action, which are at least as active as the known peptides described earlier. They are often more convenient and cheaper to prepare, and lack certain side-effects accompanying the known peptides.

The novel peptides are characterised by the general formula I:

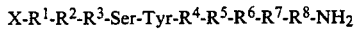

X-R$^1$-R$^2$-R$^3$-Ser-Tyr-R$^4$-R$^5$-R$^6$-R$^7$-R$^8$-NH$_2$ wherein

X represents hydrogen or a lower acyl(1–6C) group,

R$^1$ and R$^2$ represent either the same or different groups selected from D-Bal(2), D-Bal(3), D-Nal(1), D-Nal(2), D-Phe or D-Phe substituted at the phenyl moiety by one or more halogen, alkyl(1–4C), alkoxy (1–4C) or nitro groups;

R$^3$ represents D-Trp, D-Bal(2), D-Bal(3), D-Nal(1), D-Nal(2) or D-Pal, with the proviso that at least one of the symbols R$^1$ or R$^3$ represents a D-Bal(2) or D-Bal(3) group;

R$^4$ represents D-Arg, D-Lys, D-homo Arg or D-diaklyl(1–4C)-homo Arg;

R$^5$ represents L-Leu, L-Met or the alkyl(1–4C) or phenylalkyl(7–10C) ether of L-Cys, L-Ser or L-homo Ser;

R$^6$ represents L-Lys or L-Arg;

R$^7$ represents L-Pro or L-thiaprolyl, and

R$^8$ represents D-Ala or Gly.

The invention also includes the acid addition salts of the above defined peptides.

The peptides and peptide derivatives according to formula I and acid addition salts thereof are prepared in a manner that is usually applied for the synthesis of peptides. A conventional process for the preparation of the present compounds is to couple the required aminoacids by condensation either in a homogeneous phase or, for example, with the aid of a so-called solid phase, after which the peptide thus obtained is freed from its protective groups and/or solid phase.

The condensation in the homogeneous phase can be carried out as follows:

(a) condensation of an aminoacid or peptide having a free carboxyl group and protected other reactive groups with an aminoacid or peptide having a free amino group and protected other reactive groups, in the presence of a condensation agent, (b) condensation of an aminoacid or peptide having an activated carboxyl group and optionally protected other reactive groups with an aminoacid or peptide having a free amino group and optionally protected other reactive groups, or (c) condensation of an aminoacid or peptide having a free carboxyl group and optionally protected other reactive groups with an aminoacid or peptide having an activated amino group and optionally protected other reactive groups.

The activation of the carboxyl group can be carried out, inter alia, by converting the carboxyl group to an acid halide, an azide, an anhydride, an imidazolide or an activated ester, such as the N-hydroxy-succinimide, N-hydroxy-benztriazole or p-nitrophenyl ester.

The amino group can be activated by converting it to a phosphite amide or by employing the "phosphorazo" method.

The preferred methods for the above condensation reactions are: the carbodiimide method, the azide method, the mixed anhydride method and the activated esters method, as described in "The Peptides", volume I, 1965 (Academic Press), by E. Schröder and K. Lübke.

However, the compounds according to formula I can also be prepared by solid phase methods (Merrifield, J. Amer. Chem. Soc. 85, 2149 (1963)). The coupling of the aminoacides of the peptide to be prepared starts from the side which has the terminal carboxyl group. In this method a solid carrier, on which reactive groups are present or to which such groups can be attached, is required. This carrier can for example be a copolymer of styrene and divinylbenzene having reactive chloromethyl groups, or a polymeric carrier which has been made reactive with hydroxymethyl or benzylamine groups.

If, for example, a carrier possessing chloromethyl groups is used, the coupling of the first α-amino-protected aminoacid (in this case D-Ala or Gly) to the carrier takes place via an ester bond, resulting in:

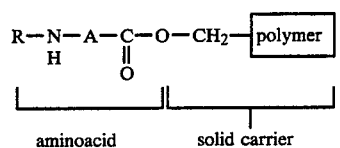

aminoacid       solid carrier wherein R is an α-amino-protective group.

If a carrier containing benzylamine groups is used, coupling takes place via an amide bond, yielding:

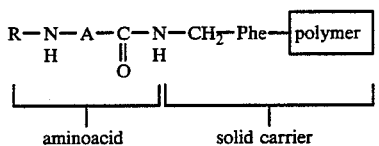

aminoacid       solid carrier

After removal of the group R, the next α-amino-protected aminoacid (in this case L-Pro or L-thiaprolyl) can be coupled; after removing the protective group of the α-amino group the next aminoacid can be coupled, etc.

After the synthesis of the desired aminoacid sequence, the complete peptide is released from the carrier. Depending on the type and nature of the carrier and the desired peptide derivative, this removal can be effected by means of hydrolysis, alcoholysis, aminolysis or hydrogenation.

In the present peptide, where the C-terminal moiety comprises a carboxamide group (cf. —D—Ala—NH$_2$ or —Gly—NH$_2$) preference is given to carriers and methods of removal which directly yield such an amide group.

The reactive groups which must not participate in the condensation reaction are protected by groups which can again be removed very conveniently, for example by hydrolysis or reduction. Thus, a carboxyl group can be protected effectively by, for example, esterification with methanol, ethanol, tertiary butanol, benzyl alcohol or p-nitrobenzyl alcohol.

Groups which can effectively protect an amino group are usually acyl groups, for example an acyl group derived from an aliphatic, aromatic, araliphatic or heterocyclic carboxylic acid, such as acetyl, benzoyl or pyridinecarboxyl, or an acyl group derived from carbonic acid, such as the ethoxycarbonyl, benzyloxycarbonyl, t-butyloxycarbonyl or p-methyloxybenzyloxycarbonyl group, or an acid group derived from a sulphonic acid, such as the benzenesulphonyl group or p-toluenesulphonyl group; however, other groups can also be used, such as substituted or unsubstituted aryl or aralkyl groups, for example benzyl and triphenylmethyl, or groups such as ortho-nitro-phenylsulphenyl and 2-benzoyl-1-methylvinyl.

The $\epsilon$-amino group of lysine and the quanidine group of arginine can also be protected. Usual protective groups in this context are a tertiary butyloxycarbonyl or tosyl group for lysine, and a nitro or MBS group for arginine. If the solid phase synthesis is used, it is also advisable to protect the (extra)hydroxyl group of serine and tyrosine.

A general synthesis for the preparation of the present peptides having the general formula I therefor comprises removing one or more protective groups and/or the solid carrier from a peptide having the general formula II:

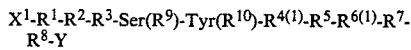

wherein $R^1$, $R^2$, $R^3$, $R^5$, $R^7$ and $R^8$ have the meanings given above;

$X^1$ has the same meaning as X but may in addition represent an N-protective group, $R^{4(1)}$ has the same meaning as $R^4$ but can in addition represent an N$^\epsilon$-protected D-lysyl group, an N$^G$-protected D-arginyl, an N$^G$-protected D-homoarginyl or an N$^G$-protected dialkyl-homoarginyl group, $R^{6(1)}$ has the same meaning as $R^6$ but can in addition represent an N$^\epsilon$-protected lysyl or an N$^G$-protected arginyl group, $R^9$ and $R^{10}$ each represent hydrogen or a protective group and Y represents an NH$_2$ group or a solid carrier which on removal can be converted to an NH$_2$ group, with the proviso that whenever Y represents an NH$_2$ group, at least one of the groups $X^1$, $R^{4(1)}$, $R^{6(1)}$, $R^9$ or $R^{10}$ is or comprises a protective group, after which, if desired, the peptide obtained, wherein X represents hydrogen, is acylated and/or the peptide obtained is converted to an acid addition salt.

The acid addition salts can be obtained directly by isolating the peptide from the desired acid medium; alternatively, the peptide obtained can subsequently be converted to an acid addition salt by reacting the peptide with an acid such as HCl HBr, phosphoric acid, sulphuric acid, acetic acid, maleic acid, tartaric acid, citric acid or polyglutamic acid.

N-Acyl derivatives by which are meant the N-terminal lower acyl(1–6C) derivatives (see the definition of X) are preferably prepared by employing, in the peptide synthesis, an aminoacid which is already provided with the relevant acyl group. This acyl group then also acts as a protective group in the peptide synthesis. In this way, the desired acyl derivative is prepared directly. However, it is also possible subsequently to introduce the desired acyl group by acylating the peptide in the conventional manner.

The N-acyl group preferably employed is an alkanoyl or alkenoyl group with 1–4C atoms, such as an acetyl, propanoyl or acrylyl group.

The peptides according to the invention have, as already stated, LH-RH antagonising properties, as a result of which they can be used both in human and veterinary medicine. The peptides according to formula I can be used to counteract an undesired effect of LH-RH. Such undesired effect of LH-RH can inter alia have occurred in hormone-dependent tumours such as benign or malignant prostate tumours and tumours in mammae, ovaries and testicles. The occurrence of acne and amenorrhoea can also be the consequence of an undesired LH-RH effect.

The peptides according to the invention can moreover be used for regulating ovulation, as a result of which they can be employed in fertility control, for example for pre-coital or post-coital contraception and for synchronisation of oestrus in animals.

The peptides according to the invention lack allergic side-effects and oedema formation which often burden the use of highly active prior art peptides.

The peptides according to the invention can be administered orally, parenterally (subcutaneously or intramuscularly), sublingually, intranasally, rectally or vaginally. Parenteral and intranasal administrations are preferred. For this purpose, the peptides are preferably mixed with pharmaceutically acceptable auxiliaries (which render the peptides suitable for parenteral or intranasal administration) resulting in solutions, suspensions (optionally via micro-encapsulation), emulsions and sprays.

Mixed with suitable auxiliaries or fillers, the present peptides can also be used in a form suitable for oral or sublingual administration, such as pills, tablets and dragees. The present peptides can moreover be administered rectally or vaginally, in the form of a suppository.

The peptides or peptide derivatives according to the invention are preferably administered in a dose of 1 $\mu$g to 1 mg per kg of body weight per day in the case of parenteral administration. For intranasal administration, a preferred daily dose is from 5 $\mu$g to 10 mg or more, especially from 10 $\mu$g to 1 mg, per kg of body weight. The recommended dosage for human administration (parenteral or intranasal) is between 0.1 and 100 mg per day; for oral, rectal and vaginal administration, the dosage is, in general, 10–1,000 times higher.

Moieties which are preferably applied in the peptides of the invention, either alone or in combination with other preferred moieties, are (a) for $R^2$ the moiety D-para-halo-Phe wherein additional halogen or alkyl groups may be present in ortho and/or meta position of the phenyl group;

(b) for $R^3$ the moiety D-Bal(3);

(c) for $R^4$ the moieties D-Arg, D-homo-Arg, or D-dialkyl(1-4C)-homo-Arg;

(d) for $R^6$ the moiety L-Arg;

(e) for $R^7$ the moiety L-Pro; and (f) for $R^8$ the moiety D-Ala;

(g) for X the moiety N-acyl, whereby the N-alkanoyl group—especially n-acetyl—is to be preferred.

A D-Bal moiety present at the positions 1 or 2 of the molecule is preferably a D-Bal(2) moiety, whereas a D-Bal moiety at position 3 is—as already stated—preferably a D-Bal(3) moiety.

In the examples which follow, and in the specification and claims, the following abbreviations are used for the aminoacid groups:

p-Glu=pyroglutamyl
Lys=lysyl
His=histidyl
Arg=arginyl
Gly=glycyl
Pro=prolyl
Met=methionyl
Ser=seryl
Leu=leucyl
Tyr=tyrosyl
Phe=phenylalanyl
Ala=alanyl
Trp=tryptophyl
Bal(2)=3-(benzothien-2-yl)-alanyl
Bal(3)=3-(benzothien-3-yl)-alanyl
Pal=3-(pyridyl)-alanyl
Pal(3)=3-(3-pyridyl)-alanyl
Nal(1)=3-(1-naphthyl)-alanyl
Nal(2)=3-(2-naphthyl)-alanyl
Har(Et)$_2$=N',N''-diethylhomoarginyl
Thz=thiaprolyl
Cys(Bzl)=cysteinyl-benzyl ether
Cys(CH$_3$)=cysteinyl-methyl ether
Cys=cysteinyl

EXAMPLES

Where no configuration of the aminoacid has been indicated, the L-form is meant.

Example 1

Ac-D-Bal(3)-D-p.Cl Phe-D-Trp-Ser-Tyr-D-Arg-Leu-Arg-Pro-D-Ala-NH$_2$

Sufficient N-ethylmorpholine to give a pH of the solution of 7 is added to a solution of 621 mg (1 mmol) of Ac-D-Bal(3)-D-p.Cl-Phe-D-Trp-OH and 1 g (~1 mmol) of H-Ser-Tyr-D-Arg-Leu-Arg-Pro-D-Ala-NH$_2$ in 10 ml of DMF. Thereafter the mixture is cooled to 0° and 200 mg of 1-hydroxybenzotriazole (1.5 mmol) and 230 mg (1.1 mmol) of dicyclohexylcarbodiimide are added successively, with stirring.

The reaction mixture is stirred for 3 hours at 5° C. and for 16 hours at room temperature. Thereafter the dicyclohexylurea formed is removed by filtration and the filtrate is evaporated down. The oil thus obtained is stirred with 25 ml of ethyl acetate, whereupon the crude product precipitates, and is filtered off. The material thus obtained is dissolved in 25 ml of t.BuOH/H$_2$O (1/1) and treated with 10 ml of ion exchanger in the acetate form (Dowex) in order to convert the decapeptide into the acetate salt form. After the ion exchanger has been filtered off, the filtrate is freeze-dried and the product thus obtained is further purified by column chromatography (SiO$_2$, eluant: butanol-pyridine-acetic acid-water 8:0.75:0.25:1).

The fractions containing the desired material are evaporated and then freeze-dried. 650 mg of product are thus obtained. Rf in butanol/pyridine/acetic acid/water (4/0.75/0.25/1)=0.53 (on SiO$_2$); $\alpha_D$ (c=0.5 in dimethylformamide)= $-3.7°$.

Example 2

The following were prepared in an analogous manner:

1. Ac-D-Bal(2)-D-p.Cl Phe-D-Trp-Ser-Tyr-D-Arg-Leu-Arg-Pro-D-Ala-NH$_2$;
2. Ac-D-p.Cl Phe-D-p.Cl Phe-D-Bal(3)-Ser-Tyr-D-Arg-Leu-Arg-Pro-D-Ala-NH$_2$;
3. Ac-D-Bal(2)-D-p.Cl Phe-D-Bal(3)-Ser-Tyr-D-Arg-Leu-Arg-Pro-D-Ala-NH$_2$;
4. H-D-Bal(3)-D-p-Cl Phe-D-Trp-Ser-Tyr-D-Arg-Leu-Arg-Pro-D-Ala-NH$_2$;
5. Ac-D-Nal(2)-D-p.Cl Phe-D-Bal(3)-Ser-Tyr-D-Arg-Leu-Arg-Pro-D-Ala-NH$_2$;
6. Ac-D-p.tert.butyl Phe-D-p.Cl Phe-D-Bal(3)-Ser-Tyr-D-Arg-Leu-Arg-Pro-D-Ala-NH$_2$;
7. Ac-D-Bal(3)-D-p.Cl Phe-D-Trp-Ser-Tyr-D-homo-Arg-Leu-Arg-Pro-D-Ala-NH$_2$;
8. Ac-D-Bal(2)-D-p.Cl Phe-D-Trp-Ser-Tyr-D-Har-(Et)$_2$-Leu-Arg-Pro-D-Ala-NH$_2$;
9. Ac-D-p.Cl Phe-D-p.Cl Phe-D-Bal(3)-Ser-Tyr-D-Lys-Leu-Pro-D-Ala-NH$_2$;
10. Ac-D-p.Cl Phe-D-p.Cl Phe-D-Bal(2)-Ser-Tyr-D-Arg-Leu-Pro-D-Ala-NH$_2$;
11. Ac-D-Nal(2)-D-p.Cl Phe-D-Bal(3)-Ser-Tyr-Har-(Et)$_2$-Leu-Pro-D-Ala-NH$_2$;
12. Ac-D-p.Cl Phe-D-p.Cl Phe-D-Bal(3)-Ser-Tyr-D-Har(Et)$_2$-Leu-Pro-D-Ala-NH$_2$;
13. Ac-D-Bal(2)-D-p.Cl Phe-D-Bal(3)-Ser-Tyr-D-Har-(Et)$_2$-Leu-Pro-D-Ala-NH$_2$.

Example 3

Ac-D-Nal(2)-D-p.Cl Phe-D-Bal(3)-Ser-Tyr-D-Arg-Met-Arg-Pro-D-Ala-NH$_2$

To a solution of 642 mg (1 mmol) of Ac-D-Nal(2)-D-p.Cl Phe-D-Bal(3)-OH and 1 g (≃1 mmol) of H-Ser-Tyr-D-Arg-Met-Arg-Pro-D-Ala-NH$_2$ (obtained by removal of the N-protective group from the Boc-Ser-Tyr-D-Arg-Met-Arg-Pro-D-Ala-NH$_2$ fragment by means of trifluoroacetic acid) in 10 ml of DMF is added sufficient N-ethylmorpholine to give a pH of 7 in the solution. This mixture is cooled to 5° C. and thereafter 200 mg of hydroxybenzotriazole (≃1.5 mmol) and 230 mg of dicyclohexylcarbodiimide (≃1.1 mmol) are added.

The reaction mixture is stirred for 3 hours at 5° C. and 16 hours at room temperature. Thereafter the diclycohexylurea formed is removed by filtration and the filtrate is concentrated by evaporation. The oil thus obtained is stirred with 25 ml of ethyl acetate, whereupon the crude product precipitates and is filtered off. The material thus obtained is dissolved in 25 ml of t.BuOH/H$_2$O (1/1) and treated with 10 ml of an ion exchanger in the acetate form (Dowex) in order to convert the decapeptide to the form of the acetate salt. After the ion exchanger has been filtered off, the filtrate is freeze-dried and the product thus obtained is further purified by column chromatography (SiO₂, eluant butanol/pyridine/acetic acid/water (Bu/Py/Ac/Wa) 8:0.75:0.25:1).

The fractions which contain the desired material are concentrated by evaporation and then freeze-dried. 720 mg of product are thus obtained. Rf in Bu/Py/Ac/Wa (4/0.75/0.25/1)=0.47 (on SiO₂); $\alpha_D$ (c=1.0, dimethylformamide)=−6.5°.

Example 4

The following decapeptides are prepared analogously.
1. Ac-D-p.Cl Phe-D-p.Cl Phe-D-Bal(3)-Ser-Tyr-D-Arg-Met-Arg-Pro-D-Ala-NH₂;
2. Ac-D-Nal(2)-D-p.Cl Phe-D-Bal(3)-Ser-Tyr-D-Arg-Cys(CH₃)-Arg-Pro-D-Ala-NH₂;
3. Ac-D-p.Cl Phe-D-p.Cl Phe-D-Bal(3)-Ser-Tyr-D-Arg-Cys(CH₃)-Arg-Pro-D-Ala-NH₂;
4. Ac-D-Bal(2)-D-p.Cl Phe-D-Bal(3)-Ser-Tyr-D-Arg-Met-Arg-Pro-D-Ala-NH₂;
5. Ac-D-Nal(2)-D-p.Cl Phe-D-Bal(3)-Ser-Tyr-D-Har-(Et)₂-Met-Arg-Pro-D-Ala-NH₂;
6. Ac-D-Nal(2)-D-p.Cl Phe-D-Bal(3)-Ser-Tyr-D-Arg-Met-Arg-Thz-D-Ala-NH₂;
7. Ac-D-Nal(2)-D-p.Cl Phe-D-Bal(3)-Ser-Tyr-D-Arg-Ser(t.Bu)-Arg-Pro-D-Ala-NH₂;
8. Ac-D-Bal(2)-D-p.Cl Phe-D-Pal(3)-Ser-Tyr-D-Arg-Met-Arg-Pro-D-Ala-NH₂;
9. Ac-D-p.Cl Phe-D-p.Cl Phe-D-Bal(3)-Ser-Tyr-D-Arg-Ser(t.Bu)-Arg-Pro-D-Ala-NH₂;
10. Ac-D-p.Cl Phe-D-p.Cl Phe-D-Bal(3)-Ser-Tyr-D-Arg-Cys(Bzl)-Arg-Pro-D-Ala-NH₂.

What is claimed is:

1. Peptides of the general formula $$X-R^1-R^2-R^3-Ser-Tyr-R^4-R^5-R^6-R^7-R^8-NH_2$$

wherein
X represents hydrogen or a lower acyl(1–6C) group,
$R^1$ and $R^2$ represent either the same or different groups selected from D-3-(benzothien-2-yl)-alanyl, D-3-(benzothien-3-yl)-alanyl, D-3-(1-naphthyl)-alanyl, D-3-(2-naphthyl)-alanyl, D-Phe or D-Phe substituted at the phenyl moiety by one or more halogen, alkyl(1–4C), alkoxy(1–4C) or nitro groups;
$R^3$ represents D-Trp, D-3-(benzothien-2-yl)-alanyl, D-3-(benzothien-3-yl)-alanyl, D-3-(1-naphthyl)-alanyl, D-3-(2-naphthyl)-alanyl or D-pyridyl-alanyl, with the proviso that at least one of the symbols $R^1$ or $R^3$ represents a D-3-(benzothien-2- or -3-yl)-alanyl group;
$R^4$ represents D-Arg, D-Lys, D-homo Arg or D-diaklyl (1–4C)-homo Arg;
$R^5$ represents L-Leu, L-Met, L-cysteine-alkyl(1–4C) or phenylalkyl(7–10C) ether, L-serine-alkyl(1–4C) or phenylalkyl(7–10C) ether or L-homoserine-alkyl(1–4C) or phenylalkyl(7–10C) ether;
$R^6$ represents L-Lys or L-Arg;
$R^7$ represents L-Pro or L-thiaprolyl, and
$R^8$ represents D-Ala or Gly,
and acid addition salts thereof.

2. A peptide according to claim 1 in which $R^8$ represents the aminoacid residue D-Ala.

3. A peptide according to claim 1 in which $R^3$ represents the aminoacid residue D-3-(benzothien-3-yl)-alanyl.

4. Pharmaceutical composition used as a LH-RH antagonist containing an effective amount of a peptide according to claim 1 in admixture with a pharmaceutical carrier.

* * * * *